United States Patent [19]

Fructus

[11] Patent Number: 5,576,064

[45] Date of Patent: Nov. 19, 1996

[54] MULTIPLE EMULSIONS

[75] Inventor: Alain Fructus, Courbevoie, France

[73] Assignee: Roussel Uclaf, France

[21] Appl. No.: 205,599

[22] Filed: Mar. 3, 1994

[30]     Foreign Application Priority Data

Mar. 11, 1993  [FR]  France .................................. 93 02795

[51] Int. Cl.$^6$ ..................................................... A61K 7/00
[52] U.S. Cl. .......................... 424/401; 252/309; 252/312; 424/400; 514/938; 514/944
[58] Field of Search ..................................... 514/938, 944; 252/309, 312

[56]              References Cited

FOREIGN PATENT DOCUMENTS

| 0345075 | 12/1989 | European Pat. Off. . |
| 2326914 | 5/1977 | France . |
| 0507693 | 10/1992 | France . |
| 2693466 | 1/1994 | France . |
| 41 36 699 | 8/1991 | Germany . |

OTHER PUBLICATIONS

Copy of Search Report (3 pages).
Copy of Patent Abstract No. JP58183611 (1 pg) Oct. 26, 1983.

*Primary Examiner*—Shelley A. Dodson
*Attorney, Agent, or Firm*—Bierman and Muserlian

[57]               ABSTRACT

A multiple emulsion to administer at least one water-soluble or liposoluble active ingredient in the form of a water/oil/water emulsion comprising a dispersed phase of a water/oil type and an aqueous dispersion medium which is a gelled aqueous phase useful as cosmetic compositions for external skin application.

4 Claims, No Drawings

MULTIPLE EMULSIONS

STATE OF THE ART

French patent no. 2,326,914 describes a multiple emulsion of the water/oil/water type containing a dispersed phase and a dispersing medium wherein the dispersed phase is an emulsion containing a water phase and an oil phase containing dissolved therein an oil soluble emulsifier and the dispersion medium is an aqueous solution containing a water-soluble emulsifier. Each phase contained an emulsifier and there often is an interaction between the said emulsifiers required for the primary emulsion and the secondary emulsion. This can result in a limited selection, uncertain stabilities due to phase inversion, transition to a single emulsion or a phase shift and therefore an average cosmetic quality.

OBJECTS OF THE INVENTION

It is an object of the invention to provide an improved multiple emulsion for water-soluble or liposoluble active ingredients and cosmetic compositions produced therefrom.

These and other objects and advantages of the invention will become obvious from the following description.

THE INVENTION

The novel multiple emulsions of the invention to administer at least one water-soluble or liposoluble active ingredient in the form of a water/oil/water emulsion are comprised of a dispersed phase of a water/oil type and an aqueous dispersion medium which is a gelled aqueous phase.

The primary water/oil emulsion is a standard type with surfactants usually used in cosmetics for this type of emulsion. However, this primary emulsion is then dispersed in an aqueous phase gelled with gelling agents which replace the emulsifiers. The primary emulsion droplets are immobilized by the flexible gel system and therefore they cannot coalesce, resulting in very high stability.

As there is no emulsifier in the external aqueous phase, the primary emulsion is not disturbed by a diffusion of emulsifiers. Altogether, a stable, multiple emulsion is obtained, produced with cosmetic raw materials which allows it to be quite harmless and agreeable to the touch.

The present invention also relates to the incorporation of water-soluble or liposoluble active ingredients in such a multiple emulsion.

The desired aims of such a multiple emulsion of the invention are to separate incompatible water-soluble active ingredients by incorporating them in two aqueous phases separated by an oily phase, which allows particular cosmetic compositions to be prepared which can progressively release the active ingredients over the skin because the structures of the multiple emulsion are destroyed more slowly than those of a single emulsion. Thus, there is an increase of the penetration of active ingredients because the internal structure of multiple emulsions and notably triple emulsions is, in some cases, similar to certain structures which act as a barrier for the skin.

A preferred multiple emulsion as described above is characterized in that the gelling agent or agents contained in the aqueous dispersion phase are selected from the group consisting of a solution based on polyglyceryl methacrylate, xanthan gum, polysaccharides, carbomers, modified carbomers, hydroxy ethyl cellulose and modified hydroxy ethyl cellulose.

A preferred multiple emulsion of the invention is characterized in that the gelling agent contained in the aqueous dispersion phase is a mixture of a solution based on polyglyceryl methacrylate, carbomers and modified carbomers. The solution based on polyglyceryl methacrylate can be Lubragel® and the modified carbomers can be Pemulen® TR1 and TR2.

Examples of such gelling agents used alone or in mixtures are used in the following preferred percentages expressed relative to the final complete formula: Lubragel®: 1 to 30%, Xanthan gum: 0.05 to 2%, Polysaccharide Amigel®: 0.05 to 2%, Carbomers: 0.01 to 2%, Modified carbomers (Pemulen®TR1 and TR2): 0.04 to 2% or Hydroxy ethyl cellulose and modified hydroxy ethyl cellulose (Amercell®): 0.05 to 3%.

Among the preferred gelling agents of the invention is the mixture of 5 to 15% by weight of LUBRAGEL®, 0.05 to 0.3% by weight of carbomers and 0.1 to 0.8% by weight of modified carbomers.

A particular subject of the present invention is a multiple emulsion, as described above, characterized in that one or more water-soluble active ingredients are incorporated in the aqueous phase of the water/oil emulsion and/or in the aqueous dispersion phase or a multiple emulsion with one or more liposoluble active ingredients incorporated in the oily phase of the water/oil emulsion.

A preferred multiple emulsion is characterized in that the water-soluble active ingredients are selected from the group consisting of sodium lactate, hafnia biolysate extracts, Klebsiella pneumonia biolysate extracts and water-soluble sun filters.

Examples of preferred water-soluble sun filters are neutralized 2-phenyl benzimidazol-5-sulfonic acid, neutralized 2-hydroxy-4-methoxybenzophenone-5-sulfonic acid, ascorbic acid, caffeine benzoate, phytic acid, mucic acid, vegetable protein hydrolysates, polygulcan, Mexican mimosa extract, chitosan, marine animal serum, hirudin extract, meristem extract, procyanodolic oligomers, yeast extracts, panthenol, centella asiatica extract and glycyrrhetinic acid.

Examples of suitable amount of water-soluble active ingredients are expressed relative to the weight of the final complete formula, neutralized 2-phenyl-benzimidazol-5-sulfonic acid: 0.5 to 8%, neutralized 2-hydroxy-4-methoxybenzophenone-5-sulfonic acid: 0.5 to 5%, Ascorbic acid: 0.5 to 10%, caffeine benzoate: phytic acid: 0.1 to 5%, mucic acid: 0.1 to 5%, 0.1 to 5%, vegetable protein hydrolysates: 0.1 to 10%, polyglucan: 0.1 to 5%, Mexican mimosa extract: 0.5 to 20%, chitosan: 0.5 to 20%, marine animal serum: 0.1 to 3%, hirudin extract: 0.5 to 10%, meristem extract: 0.1 to 5%, procyanodolic oligomers; 0.05 to 3%, yeast extracts: 0.05 to 3%, panthenol: 0.05 to 5%, centella asiatica extract: 0.05 to 3% or glycyrrhetinic acid: 0.05 to 2%.

Examples of liposoluble active ingredients are the palmitate of vitamin A, liposoluble sun filters, non-saponifiable matter of vegetable origin, vegetable oils, tocopherol acetate, natural tocopherols, farnesol, natural or synthetic ceramides.

Examples of liposoluble solar filters are octyl methoxycinnamate, isoamyl methoxycinnamate, octyl dimethyl paba, octyl salicylate, butyl methoxydibenzoyl methane, benzophenone-3, octyl triazone, ethyl 4-polyethoxy aminobenzoate and isopropyl 4-dibenzoyl methane.

The non-saponifiable matter of vegetable origin can be chosen from non-saponifiable matter of corn, karite, soya and avocado. The vegetable oils can be peroxidated or not and may be chosen from an oily mixture containing xymenic acid, essential extract of sesame oil, peroxidated corn oil, evening primrose oil, peroxidated evening primrose oil, borage oil and peroxidated borage oil. The oily mixture containing xymenic acid can be Xymenoil® which contains 50% of this acid.

Examples of such liposoluble active ingredients are, expressed relative to the weight of the final complete formula, Palmitate of vitamin A: 500 to 10,000 UI/g. Liposoluble solar filters: octyl methoxycinnamate: 0.5 to 10%, isoamyl methoxycinnamate: 0.5 to 10% octyl dimethyl paba: 0.50 to 8%, octyl salicylate: 0.5 to 5%, butyl methoxydibenzoyl methane: 0.5 to 5%, benxophenone-3: 0.5 to 10%, octyl triazone: 0.5 to 5%, ethyl 4-polyethoxy aminobenzoate: 0.5 to 10%, isopropyl-4-dibenzoyl methane: 0.5 to 5%, Non-saponifiable matter of corn, karite, soya or avocado: 0.1 to 3%,, Xymenoil®: 0.1 to 5%, essential extract of sesame oil: 0.1 to 4%, peroxidated corn oil: 0.1 to 10%, evening primrose oil: 0.1 to 10%, peroxidated evening primrose oil: 0.1 to 10%, borage oil: 0.1 to 10%, peroxidated borage oil: 0.1 to 10%, tocopherol acetate: 0.05 to 7%, natural tocopherols: 0.05 to 5%, farnesol: 0.05 to 5% and natural or synthetic ceramides: 0.01 to 10%.

Preferably, a multiple emulsion is characterized in that the volumes of the different phases are such that: the internal aqueous phase is 20 to 30% of the total composition, the oily phase is 10 to 20% of the total composition, and the external aqueous phase is 50 to 60% of the total composition.

The process for the preparation of a multiple emulsion of the invention comprises strongly stirring an aqueous phase and an oil phase to form a dispersed phase and gently stirring said dispersed phase with a gelled aqueous phase free of emulsifier to form a multiple emulsion.

Preferably, the dispersed phase is heated during the strong stirring and the gentle stirring is effected at room temperature. More preferably, the primary emulsion is produced by introducing the aqueous phase heated to 80° C. into the oily phase also at 80° C. under vigorous stirring. The second stage consists of mixing the primary emulsion and the gelled external aqueous phase at ordinary temperature under mild stirring until formation of the multiple emulsion.

A preferred multiple emulsion is characterized in that the gelling agent used to prepare the external aqueous phase is selected from the group consisting of a solution based on polyglyceryl methacrylate, xanthan gum, polysaccharides, carbomers, modified carbomers, hydroxy ethyl cellulose and modified hydroxy ethyl cellulose.

The cosmetic compositions of the invention are comprised of a multiple emulsion of the invention containing a cosmetically effective amount of a water-soluble or liposoluble active ingredient.

Examples of the excipients of the oily phase are vegetable oils such as jojoba, olive, avocado, macadamia oils, mineral oils such as oils of vaseline, hydrocarbons such as dioctyl cyclohexane or isohexadecane, esters such as ketyl palmitate or isoketyl isostearate, natural waxes such as beeswax, carnauba wax, candellila wax, semi-synthetic triglycerides such as caprylic or capric triglycerides, fatty alcohols such as ketylic or stearylic alcohol, propylene glycol esters such as propylene glycol monostearate.

Examples of other additives are antiseptics, preservatives such as parabens, bronopol, biosol, wetting agents such as glycerine, propylene glycol, sorbitol, polyoxyethylene glycol 400, as well as coloring agents in the aqueous phase.

The cosmetic compositions of the invention can be presented in all the forms used in dermatology, more particularly those which are administered by topical route. The cosmetic compositions can be presented as standard skin care products such as in the form of moisturizing creams, total-screen creams, day creams, night creams, masks or as make-up products such as foundation cream and tinted cream, or as make-up removal products or also as hygiene products.

Such compositions can be in liquid or paste form such as creams: moisturizing creams, day creams, night creams, ointments, masks, make-up creams, milks, as well as lotions and particularly sun lotions.

Such compositions may be packaged according to the case, in pots or in tubes, in glass or plastic bottles or optionally in dropping bottles or also in vials and are prepared according to the usual methods.

Preferably, a cosmetic composition is characterized in that it contains a multiple emulsion and optionally one or more usual excipients included in the multiple emulsion, as well as one or more suitable active ingredients. More preferred as a particular subject of the present invention is a cosmetic composition in the form of a sun lotion.

The invention also relates to new cosmetic compositions intended for treating blackheads characterized in that it contains a multiple emulsion and optionally one or more usual excipients as well as one or more suitable active ingredients.

The cosmetic compositions may also be to treat spotty skin, dehydrated skin, injured skin, wrinkled skin and are characterized in that they contain a multiple emulsion and optionally one or more usual excipients, as well as one or more suitable active ingredients.

In the following examples, there are described several preferred embodiments to illustrate the invention. However, it is to be understood that the invention is not intended to be limited to the specific embodiments.

EXAMPLE 1

A) A primary water/oil emulsion was prepared in the following manner: The following aqueous phase, called the internal aqueous phase, was heated to 80° C.:

| | |
|---|---|
| demineralized water | 26.52 g |
| methylparaben | 0.1 g |
| magnesium sulfate | 0.28 g |
| glycerine 30° Be | 0.8 g |
| 0-cymen-5-ol | 0.04 g |

The following oily phase was also heated separately to 80° C.:

| | |
|---|---|
| glyceryl isostearate | 2.0 g |
| polyethoxylated hydrogenated ricin oil (7 moles) | 0.2 g |
| capric/caprylic triglycerides | 8.2 g |
| propylparaben | 0.06 g |
| volatile silicone oil | 1.6 g |

The aqueous phase was dispersed into the oily phase at 80° C. by stirring vigorously for 5 minutes and then the mixture was slowly cooled down to 25° C.

B) The multiple emulsion was prepared in the following manner:

The primary emulsion obtained in a) was then dispersed in the following aqueous phase, called the external aqueous phase, by mixing gently at ambient temperature:

| | |
|---|---|
| demineralized water | s.q.f. 100.0 g |
| Lubragel MS ® | 15.0 g |
| Pemulen TR1 ® | 0.6 g |
| Carbopol 980 ® | 0.03 g |
| tetrasodium EDTA | 0.054 g |
| methylparaben | 0.216 g |
| imidazolidinyl urea | 0.216 g |
| pure soda | 0.125 g |
| perfume | 0.2 g |

Characterization by Rheological Study

The rheological study was carried out using a CSL 100 viscometer with imposed stress (RHE0, 91 Champlan) at 25°±1° C. The geometry of the shearing action used was a cone/plate geometry (diameter=4 cm, cone angle=2°) and allowed analyses by sweeping under stress from 0.6 Pa to 600 Pa to be carried out. The displacement sensor had a resolution of $10^{-5}$ rd and the results were analyzed with Carri50 software. Two types of studies were carried out:

1—Oscillatory viscoelastic analysis (dynamic)

This analysis was carried out in such a way as to provide a very precise and characteristic signature of the "at rest" structure of the examples. In this type of analysis, the sample was subjected to a pulsed sinusoidal shearing action=2N (N: frequency of shearing action), which was defined by the following expressions of shear stress and deformation.

shear stress $\tau$ (t)=$_0$cos t shear deformation $\epsilon$ (t)=$\epsilon_o$cos(wt+$\delta$)

These experiments allowed a certain number of rheological variables characteristic of the sample to be defined.

shear modulus $G^*=\tau_0/\epsilon_0$
phase shift (stress/deformation) $\delta$
loss modulus $G''=G^*\sin\delta$ During this experiment, sweeping under stress at a fixed frequency was carried out during which the evolution of $G^*$, $\delta$, $G''$ was recorded. A plateau area characteristic of a non-modified structure (structure at rest) was obtained for values of the stress which were lower than a certain critical value $(\tau_0)_c$ or the stress for which $G''$ represents a maximum.

The dynamic rheological variables retained as characteristic sizes of the structure were:

the average value of $G^*$ calculated at the level of the plateau- the average of $\delta$ calculated at the level of the plateau,
the value of the critical stress $(\tau_0)_c$
the value of the critical deformation $(\epsilon_0)_c$.

The values indicated in the table below were obtained for the multiple emulsion of Example 1.

| | |
|---|---|
| $G^*$ (Pa) | 155 |
| $\delta$ (deg) | 10 |
| $\tau c$ (Pa) | 72 |
| $\epsilon c$ | 0.78 |

2—Permanent flow system analysis

This type of test was intended to provide information on the role of the shearing action in an optional destructuring and on its more or less reversible character. This experiment was carried out under shearing conditions which reproduced those which would be optionally implemented during use on the skin (maximal shearing speed $\epsilon$ max=$10^3$ S$^{-1}$). For this type of analysis, permanent flow tests were carried out during which the sample will be sheared according to successively increasing stress cycles (rise), constant stress cycles (plateau) and decreasing stress cycles (descent).

This succession of stress cycles was used on a sample according to the protocol:
a) shearing cycle on a "new" sample having undergone no pre-shearing action,
b) shearing cycle on the same sample after leaving at rest for one hour,
c) shearing cycle on the same sample after a one hour pre-shearing action at a speed of $10^3$ S$^{-1}$.

The quantitative treatment of the rheogram was carried out by looking for the best adjustment which was usually provided by the CROSS model. This permanent flow system analysis was completed by oscillatory rheological analyses which had been carried out on the same sample, before or after each shearing cycle. More precisely, four sweeps under stress at a fixed frequency and temperature (N=1 Hz, t=20° C.) were carried out according to the following sequence:

a': on the "new" sample, before cycle a,
b': immediately after cycle a,
c': immediately after cycle b,
d': immediately after cycle c.

For the product of the multiple emulsion of Example 1, the results of oscillatory rheological analyses (rings a', b', c' and d') which were carried out on the same sample before and after each shearing cycle (rings a, b, c) and the average values of $G^*$ indicated in the table below were obtained:

| Sweep | $G^*$ (Pa) |
|---|---|
| Cycle a' | 133 |
| Cycle b' | 111 |
| Cycle c' | 105 |
| Cycle d' | 117 |

CONCLUSION

A relative variation of $G^*$ was observed which was very low and of similar size to the relative variations of the parameters of Cross's law. The shearing action exerted a quite negligible influence on the samples (during the interval of time the stresses were used). This was due to a useful property related to the stability of the multiple emulsion obtained in Example 1.

EXAMPLE 2

A) A primary water/oil emulsion was prepared in the following manner:

The following aqueous phase called the internal aqueous phase was heated to 80° C.:

| | |
|---|---|
| demineralized water | 26.52 g |
| methylparaben | 0.1 g |
| magnesium sulfate | 0.28 g |
| glycerine 30° B | 0.8 g |
| 0-cymen-5-ol | 0.04 g |
| The following oily phase was heated separately to 80° C.: | |
| gylceryl isostearate | 2.0 g |
| PEG-7 hydrogenated Castor Oil | 0.2 g |
| capric/caprylic triglycerides | 8.2 g |
| propylparaben | 0.06 g |
| mineral oil/quaternium 18 hectorite/ propylene carbonate | 0.2 g |
| cyclomethicone | 1.6 g |

The aqueous phase was dispersed in the oily phase at 80° C. by stirring vigorously for 5 minutes and then, the mixture was slowly cooled to 25° C.

B) The multiple emulsion was prepared in the following manner:

The primary emulsion obtained in a) was then dispersed in the following aqueous phase called the external aqueous phase by mixing gently at ambient temperature:

| | |
|---|---|
| polyglyceryl methacrylate/propylene glycol | 15.0 g |
| acrylates/C10–30 alkyl acrylate crosspolymer | 0.6 g |
| carbomer 980 | 0.03 g |
| tetrasodium EDTA | 0.054 g |
| methylparaben | 0.216 g |
| imidazolidinyl urea | 0.216 g |
| sodium hydroxide | 0.125 g |
| water | s.q.f. 100.0 g |

EXAMPLE 3

A) A primary water/oil emulsion was prepared in the following manner:

The following aqueous phase called the internal aqueous phase was heated to 80° C.:

| | |
|---|---|
| demineralized water | 26.52 g |
| methylparaben | 0.1 g |
| magnesium sulfate | 0.28 g |
| glycerine 30° B | 0.8 g |
| 0-cymen-5-ol | 0.04 g |

The following oily phase was heated separately to 80° C.:

| | |
|---|---|
| gylceryl isostearate | 2.0 g |
| polyethoxylated hydrogenated ricin oil (7 moles) | 0.2 g |
| capric/caprylic triglycerides | 8.2 g |
| propylparaben | 0.06 g |
| volatile silicone oil | 1.6 g |

The aqueous phase was dispersed in the oily phase at 80° C. by stirring vigorously for 5 minutes and then, the mixture was slowly cooled to 25° C.

B) The multiple emulsion was prepared in the following manner:

| | |
|---|---|
| demineralized water | s.q.f. 100.0 g |
| Lubragel MS ® | 15.0 g |
| Pemulen TR1 ® | 0.6 g |
| Carbopol 980 ® | 0.03 g |
| hafnia biolysate | 0.03 g |
| tetrasodium EDTA | 0.054 g |
| methylparaben | 0.216 g |
| imidazolidinyl urea | 0.216 g |
| pure soda | 0.125 g |
| perfume | 0.2 g |

EXAMPLE 4

The product of Example 4 was prepared by the same process of Example 3, incorporating as active ingredients 3.2 g of water-soluble sun filters in the primary water/oil emulsion in place of the palmitate of vitamin A and 2.8 g of liposoluble sun filters in the preparation of the multiple emulsion in place of the hafnia biolysate.

EXAMPLE 5

Triple W/O/W emulsion

The following primary W/O emulsion was prepared which was then slowly cooled to ambient temperature:

| | |
|---|---|
| glyceryl isostearate | 2.0 g |
| 70E polyoxyethylene hydrogenated ricin oil | 0.2 g |
| caprylic/capric triglycerides | 8.2 g |
| propyl p-hydroxybenzoate | 0.06 g |
| volatile silicone oil | 1.6 g |
| palmitate of vitamin A at 1.7 M UI/g | 0.12 g |
| demineralized water | 26.52 g |
| methyl p-hydroxybenzoate | 0.1 g |
| magnesium sulfate | 0.28 g |
| glycerine 30° codex | 0.8 g |
| 0-cymen 5-ol | 0.04 g |

The multiple emulsion was then obtained by slowly dispersing the primary emulsion in the following aqueous phase at ambient temperature:

| | |
|---|---|
| Lubragel MS ® | 15.0 g |
| carboxyvinylic polymer | 0.03 g |
| tetrasodium EDTA | 0.054 g |
| methyl p-hydroxybenzoate | 0.216 g |
| imidazolidinyl urea | 0.216 g |
| pure sodium hydroxide | 0.125 g |
| hafnia biolysate | 0.02 g |
| demineralized water | s.q.f. 100.0 g |

EXAMPLE 6

The product of Example 6 was prepared by the process of Example 3, incorporating as active ingredient 6 g of hydrated sodium lactate in place of the hafnia biolysate. In this way, several types of active ingredients were incorporated in a multiple emulsion according to preparations indicated above in Examples 3 to 6, and as summarized in the following table:

| | Internal aqueous phase | Oily phase | External aqueous phase |
|---|---|---|---|
| 3 | Hafnia biolysate | — | — |
| 4 | Hydrosoluble sun filter | Liposoluble sun filter | — |
| 5 | — | Palmitate of vitamin A | — |
| 6 | Hydrating sodium lactate | — | — |

EXAMPLE 7

A) A primary water/oil emulsion was prepared in the following manner:

| | |
|---|---|
| demineralized water | 35.5 g |
| methylparaben | 0.1 g |
| magnesium sulfate | 0.28 g |
| Glycerine 30° B | 2.0 g |
| 0-cymen-5-ol | 0.04 g |
| extract of *Klebsellia pneumoniae* biolysate | 0.005 g |
| The following oily phase was heated separately to 80° C.: | |
| glyceryl isostearate | 2 g |
| ketyl dimethicone copolyol (ABIL EM 90 ®) | 0.4 g |
| triglycerides 5545 | 1.0 g |

-continued

| volatile silicone oil | 2.0 g |
| borage oil | 2.0 g |

The aqueous phase was dispersed in the oily phase at 80° C. by stirring vigorously for 5 minutes and then, the mixture was slowly cooled to 25° C.

B) The multiple emulsion was prepared in the following manner:

The primary emulsion obtained in a) was dispersed in the following aqueous phase called the external aqueous phase by mixing gently at ambient temperature:

| lubragel MS (R) | 8 g |
| modified hydroxyethyl cellulose (AMERCEL HM 1500 ®R) | 0.6 g |
| tetrasodium EDTA | 0.054 g |
| methylparaben | 0.216 g |
| imidazolidinyl urea | 0.125 g |
| perfume | 0.2 g |
| glycolic extract of Mexican mimosa | 5.0 g |
| demineralized water | s.q.f. 100 g |

CLINICAL STUDY

I—Test for innocuousness and measurement of sun protection factor

1—Protocol:

a) Primary cutaneous irritation

The product studied was applied as is in an occlusive buffer onto the normal and incised flanks of 6 rabbits at a dose of 0.5 ml according to the following protocol:

The fur of 6 rabbits was shaved 24 hours before the test on the back and flanks; and using a vaccinator, 3 parallel scarifications (about 3 cm long, spaced 0.5 cm apart were produced on the right flank of each animal. The other flank was kept intact and the product was deposited on 2 square pieces of Codex hydrophilic gauze with 8 thicknesses of 2.5 cm per side. One piece of gauze was applied to each of the flanks and a 10 cm wide expandable band was wrapped around the trunk of the animal. The rabbits were put back in their cage for 24 hours at the end of which the bandage and the 2 pieces of gauze were removed.

b) Ocular irritation

After having verified that the 6 rabbits had healthy eyes with no defects, the product was dropped as is at a rate of 0.1 ml into the averted lower eyelid of the right eye of each rabbit. The eyelids were kept closed for about 10 seconds to avoid the loss of the product and to improve contact. After holding in place for an hour, the animals were placed in their individual cages.

2—Results:

a) Primary cutaneous irritation

Under the experimental conditions, the product of Example 4 applied as is onto the skin caused the appearance of a slight irritation reaction (erythema) on the intact and scarified skin respectively of 3 to 6 animals. These phenomena appeared to be almost totally reversible 48 hours later. No notable structural modification was observed. The primary cutaneous irritation factor calculated according to the official method was equal to 0.5. This factor leads the product of Example 4 to be classified in the substances which do not irritate the skin.

b) Ocular irritation

Under the experimental conditions used for dropping the product of Example 4 as is in the eye, it caused the appearance of a slight irritation reaction localized at the level of the conjunctiva of 6 animals (enanthema, chemosis and profuse weeping) and the iris of 4 animals (congestion). These phenomena appeared to be reversible after 24 hours for the iris and after 72 hours for the conjunctiva.

The maximum ocular irritation factor (MaOI) was obtained 1 hour after dropping in the eye and was equal to 15.3. The average ocular irritation factors were respectively: 3.7 after 24 hours, 1 after 48 hours and 0 from 72 hours onwards. These factors lead to the product of Example 4 being classified in the substances which were very slightly irritating to the eye. By comparison, the result for a cream without an emulsifier containing the same sun filters at the same doses was 1.2, slightly irritating for primary cutaneous irritation and very slightly irritating for ocular irritation.

CONCLUSION

The multiple emulsion therefore appears particularly well tolerated by the skin.

II—Test for measuring the sun protection factor.

1—Experimental protocol:

Determination of the UVB Radiation Source

The apparatus used was a 150 W xenon lamp as UVB/UVA radiation. The UV radiation was conducted through 6 optical filters fitted at their end with two 1 mm thick fibers, WG 320 and UG 11, allowing a continuous spectrum of wavelengths between 290 and 390 nm to be obtained. Each spot had an 8 mm diameter spherical form. The energy emitted by each fiber was regulated by means of a screen and the 6 fibers delivered energies whose values increased according to a geometric progression at the rate of 1.25. The values displayed by the apparatus were expressed in MED/min.

Preliminary Medical Check

Before any application of product, each subject underwent a medical check intended to determine his/her phototype and to verify the absence of any dermatosis or any local therapeutic treatment.

Experimental Areas

The study of the minimum erythematous dose was carried out for each subject on the skin of the dorsal region. The products being tested were applied on the dorso-lumbar area on either side of the spinal column.

Quantities of Products Applied

The products were applied over a 35 cm$^2$ area of the skin. 2 mg of the product were applied per cm$^2$ of skin on the area thus defined and accurately located.

Study of the Minimum Erythematous Dose (MED) on Unprotected Skin

The MED was studied for each of the subjects before any application of product. It corresponded to the first energetic dose of UVB capable of inducing a "non-ambiguous" erythema of the unprotected skin, covering all or most of the irradiated area. This evaluation was made between 20 and 24 hours after the exposure of the subjects to the irradiation under a "daylight" type lighting.

Actual Test

About twenty minutes after the thermal stabilization of the lamp, exposure was carried out approximately 15 minutes after application of the product. For each of the products, the 6 doses of UV radiation applied were determined by a geometric progression at the rate of 1.25. 20 to 24 hours after this exposure, an evaluation of the cutaneous erythema was made under a "daylight" type lighting. The first energetic dose of UVB inducing a "non-ambiguous" erythema of the protected skin covering all or most of the irradiated area was recorded.

Expression of the Results

The average protection factors were calculated from the individual protection coefficient Qi corresponding for each subject to the ratio between the MED obtained on the protected skin and the MED obtained on the unprotected skin (Schultze method). The Sun Protection Factor of the product was calculated by the arithmetical method and expressed by the average and standard deviation obtained from individual results.

As a function of the factor obtained, the product was classified in one of the following categories:

Minimum protection for SPF's comprised between 2 and 4,

Average protection for SPF's comprised between 4 and 6,

High protection for SPF's comprised between 6 and 8,

Maximum protection for SPF's comprised between 8 and 15,

Ultra protection for SPF's higher than 15.

2—Results

Study of the MED Before Application of the Products

The apparatus delivered 6 UV radiation energies which increase according to a geometric progression at the rate of 1.25 and were expressed in MED/min, that is:

E=0.66–0.82–1.02–1.28–1.60–2.00

The exposure time t1 (sec) was chosen for each of the subjects as a function of their phototype. The energy E1 for which a clear erythema was obtained was noted in MED/min. The initial MED D1 for each subject was calculated according to the formula:

$$D1 = \frac{t1 \times E1}{60}$$

Evaluation of the Sun Protection Factors

As previously, the apparatus delivered 6 UV radiation energies which increase according to a geometric progression at the rate of 1.25 and were expressed in MED/min, that is:

E=0.66–0.82–1.02–1.28–1.60–2.00

Determination of the exposure time t2 (sec.) was carried out as a function of the initial MED D1 of each subject and of the coefficient of assumed maximum protection of the product to be tested (i.e. n). In the present case:

n=7 for the standard 11 for the product of Example 4.
The subject was exposed to a maximum energy of:

xD1=7×D1 for the standard 11×D1 for the product of Example 4.

For the maximum energy emitted by the lamp being fixed at 2 MED/min to obtain n×D1, the following exposure time was required:

$$t2 = \frac{n \times D1 \text{ min}}{2} \text{ or } 30 \, nD1 \text{ sec.}$$

that was 210 D1 sec. for the standard
that was 330 D1 sec. for the product of Example 4.

The energy E2 with which a clear erythema was obtained was noted in MED/min. The MED D2 after application of the products for each subject was calculated according to the formula:

$$D2 = \frac{t2 \times E2}{60}$$

The approximate sun protection factor was calculated in the following manner:

$$S.P.F = \frac{D2}{D1}$$

Under the test conditions, the approximate average sun protection factor of the standard defined by FDA was equal to: 3.4±0.8. The test was validated since the sun protection coefficient obtained with the standard was situated within the limits accepted for the method (between 3.1 and 5.3). The average sun protection factor of the product of Example 4, tested under the same conditions was equal to: 6.4±0.9. This same sun protection factor was determined for the product of Example 4, 2 hours after application, to test the residual existence of the product. Under these conditions the sun protection factor was equal to: 6.1±1.2

CONCLUSION

These results therefore showed the effectiveness in terms of sun protection of the product of Example 4. The test for innocuousness described above was carried out for the product of Example 4 and this product was classified as very slightly irritating for ocular irritation and as non-irritating for primary cutaneous irritation which is an excellent result relative to a standard sun protection product. The sun protection factor measured was comparable to that obtained with a standard emulsion containing the same filters at the same dose.

B—Test for comedolytic activity

The animal chosen for the test for comedolytic activity was the female Hairless Rhino (hr rh) mouse, this choice being due to the fact that the skin of such an animal has a high density of comedones of large diameter and with a narrow orifice. The use of comedolytic agents on the skin of the animal caused the opening of the orifice of the comedo, the release of the keratic substance and the sebum that it contains. Two groups were made up, each group containing 6 mice which were 6 weeks old at the start of the test and weighing on average 18 grams each. The first group was made up of mice treated with distilled water (negative control group), the second group was made up of mice treated with the product being studied. Such a treatment consisted of a topical application of the product studied on the interscapular area at a dose of 0.02 ml, 5 days out of 7 for 21 days.

The animals were sacrificed at the end of the three weeks of treatment, 24 hours after the last application. Biopsies of the skin were then taken from the treated areas of the animals and from these biopsies, sections were prepared with a view to a standard morphometric study carried out by methods known to one skilled in the art. The following parameters were measured:

| | |
|---|---|
| diameter of the opening of the comedo at the surface | that is d |
| diameter of the comedo | that is D |
| comedonian profile | that is R = d/D |

The ratio R=d/D allowed the action of the comedolytic agents to be quantified. The percentage of inhibition of the comedones was calculated for the product being studied relative to the negative control, that is the following ratio:

$$20\% \text{ inhibition} = \frac{(R \text{ product} - R \text{ negative control}) \times 100}{R \text{ negative control}}$$

The test for keratolytic activity described above was carried out for the product of Example 5 and the product of Example 5 was compared with two preparations also containing vitamin A, that is a water-silicone emulsion and an emulsion with two phases prepared as indicated hereafter. Thus, for the product of Example 5, 53% of the keratolytic activity of acid vitamin A (Alberel gel) used as the standard was obtained, while with the water/silicone emulsion 20% was obtained, and with the two-phase emulsion 39% was obtained. The results clearly show the advantage of the preparation of the invention illustrated by Example 5 on standard preparations.

Preparation of the Products Used in the Clinical Study

| Two-phase emulsion | The following emulsion was prepared: |
|---|---|
| stearylic alcohol | 1.0 g |
| ketylic alcohol | 2.0 g |
| ketearyl octanoate | 4.0 g |
| polysorbate 60 | 4.0 g |
| sorbitan stearate | 4.0 g |
| caprylic/capric triglycerides | 3.0 g |
| karite butter | 3.0 g |
| oleyl acetate (anti-lipase) | 2.0 g |
| silicone oil | 0.5 g |
| tocopherols | 0.05 g |
| demineralized water | s.q.f. 100.0 g |
| carboxyvinylic polymer | 0.3 g |
| preservatives | 0.7 g |
| Lubragel MS | 5.0 g |
| palmitate of vitamin A 1.7 M UI/g | 0.12 g |
| sodium hydroxide 10% | 0.3 g |
| perfume | 0.2 g |
| hafnia biolysate | 0.02 g |

Water/Silicon Emulsion

The following emulsion was prepared at 60° C.:

| | |
|---|---|
| demineralized water | s.q.f. 100.22 g |
| sodium chloride | 0.8 g |
| pure citric acid | 0.01 g |
| methylparaben | 0.25 g |
| preservatives | 2.0 g |
| hafnia biolysate | 0.02 g |
| isoketyl stearate | 3.0 g |
| arlacel 83 | 0.8 g |
| hydrogenated ricin oil | 0.3 g |
| elfacos ST 9 ® | 2.0 g |
| oleyl acetate (anti-lipase) | 2.0 g |
| propylparaben | 0.15 g |
| silicon DC 3225 ® | 9.0 g |
| volatile silicone | 4.0 g |
| bronopol | 0.05 g |
| palmitate of vitamin A 1.7 M UI/g | 0.12 g |
| perfume | 0.3 g |

Various modifications of the compositions and method of the invention may be made without departing from the spirit or scope thereof and it is to be understood that the invention is intended to be limited as defined in the appended claims.

What is claimed is:

1. A multiple emulsion to administer at least one water-soluble or liposoluble ingredient in the form of a water/oil/water emulsion consisting essentially of a dispersed phase of a water/oil and an aqueous dispersion medium which is a gelled aqueous phase, the aqueous dispersion phase contains a gelling agent comprised of a polyglyceryl methacrylate solution, carbomers and modified carbomers, the polyglyceryl methacrylate being 5 to 15% by weight of the total composition.

2. A multiple emulsion of claim 1 wherein the aqueous phase of the water/oil emulsion and/or the aqueous dispersion phase contains at least one water-soluble active ingredient.

3. A multiple emulsion of claim 2 wherein the water soluble active ingredient is selected from the group consisting of sodium lactate, hafnia biolysate extracts, Klebsellia pneumonia biolysate extracts and water soluble sun filters.

4. A multiple emulsion of claim 1 comprising 20 to 30% by weight of the internal aqueous phase, 10 to 20% by weight of oil phase and 50 to 60% by weight of the aqueous dispersion phase, based on the weight of the total composition.

* * * * *